(12) United States Patent
Robertson et al.

(10) Patent No.: US 6,403,300 B1
(45) Date of Patent: Jun. 11, 2002

(54) MONOCLONAL ANTIBODIES FOR DETECTION OF FRIEND MURINE LEUKEMIA VIRUS

(75) Inventors: Michael N. Robertson, Hamilton; Bruce Chesebro, Corvalis, both of MT (US); Masaaki Miyazawa, Sendai (JP); William J. Britt, Birmingham, AL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/694,302

(22) Filed: May 2, 1991

Related U.S. Application Data

(63) Continuation-in-part of application No. 07/528,714, filed on May 24, 1990, now abandoned.

(51) Int. Cl.$^7$ .................................................. C12Q 1/70
(52) U.S. Cl. .................... 435/5; 435/339.1; 530/388.35
(58) Field of Search ................................ 435/5, 240.27, 435/339.1; 436/548, 813; 530/388.35; 424/89

(56) References Cited

U.S. PATENT DOCUMENTS 5,045,447 A * 9/1991 Minson .......................... 435/5

OTHER PUBLICATIONS

Chesebro et al., Virology 112:131–144, 1981.*
Earl et al., Science 234: 728–731, 1986.*
Material Transfer Agreement to Dr. Marc Sitbon, France, Feb. 13, 1990, for hybridoma cell line 720.
Material Transfer Agreement to Rex Risser, Madison, Wisconsin, Feb. 20, 1990, for hybridoma cell lines 48 and 720.
Material Transfer Agreement to Steven Specter, Tampa, Florida, Feb. 28, 1991, for monoclonal antibody 720.

* cited by examiner

Primary Examiner—Donna Wortman
(74) Attorney, Agent, or Firm—Townsend and Townsend and Crew LLP

(57) ABSTRACT

The present invention relates to Friend murine leukemia virus (F-MuLV) specific monoclonal antibodies, or binding fragments thereof, specific for an antigenic determinant of a gp85 envelope precursor protein characteristic of a methanol-fixed F-MuLV infected cell. The invention also relates to hybridomas resulting from the fusion of myeloma cells and spleen cells, which hybridomas produce a Friend murine leukemia virus (F-MuLV) specific monoclonal antibody specific for an antigenic determinant of a gp85 envelope precursor protein characteristic of a methanol-fixed F-MuLV infected cell. The invention further relates to kits containing the above-described monoclonal antibodies.

10 Claims, 5 Drawing Sheets

US 6,403,300 B1

MONOCLONAL ANTIBODIES FOR DETECTION OF FRIEND MURINE LEUKEMIA VIRUS

This application is a continuation-in-part of application Ser. No. 07/528,714, filed May 24, 1990, abandoned.

BACKGROUND OF THE INVENTION

1. Field of the Invention

The present invention relates, in general, to monoclonal antibodies. In particular, the present invention relates to monoclonal antibodies that recognize Friend murine leukemia virus.

2. Background Information

Several monoclonal antibodies which react with the Friend murine leukemia virus (F-MuLV) and related retroviruses have been produced (CHESEBRO, B. et al. (1983a) Virology 127, 134–148). These antibodies have been used to titrate and distinguish a mixture of ecotropic F-MuLV and dual-tropic Friend mink cell focus-inducing (MCF) viruses in a focal infectivity assay (FIA) using indirect membrane immunofluorescence to detect foci of infected live cells (SITBON, M. et al. (1985) Virology 141, 110–118). However, with immunofluorescence microscopy it has often been difficult to find low power (10×) objectives with sufficient light gathering capacity to facilitate visualization of foci. Higher magnifications can be used, but this greatly increases the labor of scanning culture wells to count foci of viral infection. These problems can be overcome by using immunoperoxidase, rather than immunofluorescence in the detection of foci, but in this situation it is desirable to carry out tests on methanol-fixed cells both to eliminate endogenous peroxidase and to allow detection of antigens in the cytoplasm of infected cells. Furthermore, the use of fixed cells aids greatly in the convenience of performing assays since multiple assays can be prepared and stored for processing at a later time. However, monoclonal antibodies generated against protein antigens in their native state frequently will not recognize the viral antigens after fixation.

The present invention provides monoclonal antibodies selected specifically for reactivity with methanol-fixed viral antigens. These monoclonal antibodies were shown to be highly effective in titration of virus by a focal infectivity assay using an indirect immunoperoxidase detection system. In addition, one of these antibodies was found to be very useful in immunohistochemical detection of viral antigen by light microscopy and immunoelectronmicroscopy.

SUMMARY OF THE INVENTION

It is an object of the invention to provide hybridomas capable of producing monoclonal antibodies specific for antigenic sites on methanol-fixed F-MuLV infected cells.

It is another object of the invention to provide monoclonal antibodies that recognize epitopes of a Friend murine leukemia virus specific antigen.

It is a further object of the invention to provide diagnostic test kits comprising the above-described monoclonal antibodies.

These objects, and others which will be apparent to those skilled in the art from the following detailed description, have been accomplished by providing novel monoclonal antibodies which are specific for antigens characteristic of methanol-fixed F-MuLV infected cells.

In one embodiment, the present invention relates to hybridomas, resulting from the fusion of myeloma cells and spleen cells, which produce Friend murine leukemia virus specific monoclonal antibodies that form an immune complex with antigenic determinants of methanol-fixed F-MuLV infected cells.

In another embodiment, the present invention relates to Friend murine leukemia virus specific monoclonal antibodies specific for an antigenic determinant characteristic of a methanol-fixed F-MuLV infected cell.

In a further embodiment, the present invention relates to a diagnostic kit comprising
i) the above-described monoclonal antibodies, and
ii) a conjugate comprising a binding partner of the monoclonal antibody and a label; alternatively the kit can comprise a conjugate comprising the above-described monoclonal antibody and the label.

DETAILED DESCRIPTION OF THE INVENTION

Figure 1:
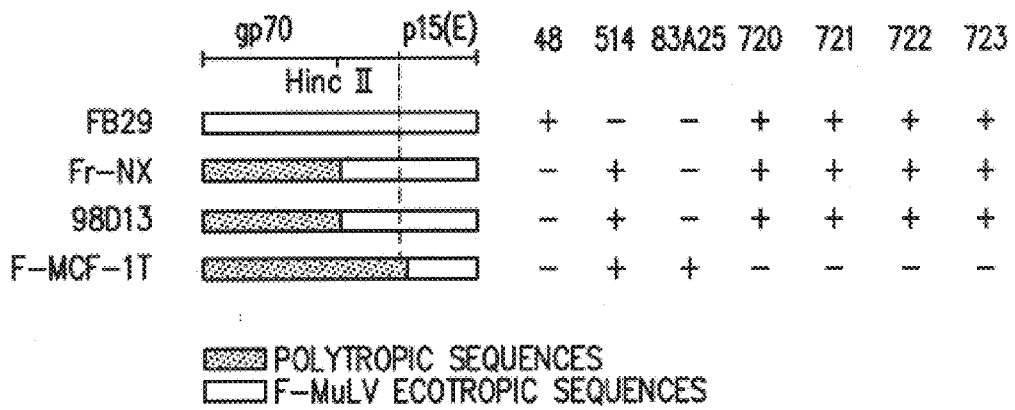
FIG. 1. Reactivity of monoclonal antibodies with recombinant MCF viruses. The structure of the envelope proteins of recombinant MCF viruses is shown with portions derived from endogenous polytropic sequences in black and portions derived from F-MuLV ecotropic sequences in white. The data are derived from the sequences of the DNA proviruses. Antibody 48 (CHESEBRO, B. et al. (1981). Virology 112, 131–144) is specific for F-MuLV envelope, antibody 514 (CHESEBRO, B. et al. (1983a). Virology 127, 134–148) reacts with the polytropic-derived portion of the envelope of all MCF viruses tested. Antibody 83A25 (EVANS, L. H. et al. (1990). J. Virol. 64) reacts with all MuLV, except F-MuLV.

The present invention relates to Friend murine leukemia virus (F-MuLV) specific monoclonal antibodies, or binding fragments thereof, specific for an antigenic determinant of a gp85 envelope precursor protein characteristic of a methanol-fixed F-MuLV infected cell. Monoclonal antibodies 720, IgG1; 721, IgG2a; 722, IgG1; and 723, IgG3, are preferred.

The monoclonal antibodies of the invention are produced by hybridomas, advantageously murine hybridomas, that can be prepared and selected as described in the Examples that follow. For example, mice can be immunized by tail scratch with a recombinant vaccinia virus expressing the gp85 envelope protein of F-MuLV (specifically, virus P4-4), a booster inoculation can be given, and, after a time sufficient to induce an immune response, the mouse is sacrificed and the spleen and/or lymph cells are obtained and fused, advantageously, with myeloma cells (preferably, murine cells or X63-Ag8.653 cells), using known techniques. The resulting cells, which include the fused hybridomas, are allowed to grow in a selective medium, such as HAT-medium, and the surviving cells are grown in such medium using limiting dilution conditions. The cells are grown in a suitable container, e.g., microtitre wells, and the supernatants are screened for monoclonal antibodies having the desired specificity.

The invention also relates to useful binding fragments of the Friend murine leukemia virus (F-MuLV) specific monoclonal antibodies. The antibody fragments are obtained by conventional techniques. For example, useful binding fragments can be prepared by digestion of the antibody using papain or pepsin.

While the above-specified examples of the antibodies of the invention are of the IgG class and are from a murine source, this is not meant to be a limitation. The specified antibodies and antibodies functionally equivalent thereto (that is, capable of binding to the above-described gp85 envelope protein antigens characteristic of methanol-fixed F-MuLV infected cells) whether from a murine source, mammalian source, including human, or other sources, or combinations thereof, are included within the scope of this invention, as are antibodies of other classes such as IgA, IgM, IgE, and the like, including isotypes within such classes.

Various conventional methods exist for isolation and purification of the monoclonal antibodies, so as to free monoclonal antibodies from other proteins and other contaminants (see, for example, Goding, in *Monoclonal Antibodies: Principals and Practice,* Chapter 4, 1986; the entire contents of which document is hereby incorporated by reference and relied upon).

The invention also relates to a diagnostic kit for use in detecting the presence of F-MuLV containing cells in a biological sample, which kit is based, for example, on the method described above. In one embodiment, the diagnostic kit comprises (i) the monoclonal antibody or antibodies (or binding fragment(s) thereof) as defined above, and (ii) a conjugate of a specific binding partner for the monoclonal antibody and a label capable of producing a detectable signal. Reagents, such as ancillary agents, for example, buffering agents and protein stabilizing agents and the like, can also be included. The diagnostic kit can further include, where necessary, other members of the signal producing system, of which system the label is a member, agents for reducing background interference in a test, control reagents, and apparatus for conducting a test. In another embodiment, the diagnostic kit comprises a conjugate of a monoclonal antibody or antibodies of the invention and a label capable of producing a detectable signal. Ancillary agents as mentioned above can also be present.

The present invention is described in further detail in the following non-limiting examples.

EXAMPLES

The following protocols and experimental details are referenced in the Examples that follow:

Mice. B10.A(2R), BALB/c and A.BY mice were purchased from the Jackson Laboratory, Bar Harbor, Me. (B10.A(2R)×A.BY)F, mice and IRW (CHESEBRO, B. et al. (1983b) *Virology* 128, 221–233) mice were bred at Rocky Mountain Laboratories.

Cell Lines. Three fibroblast-like cell lines were used to grow virus: Dunni cells, a tail culture from the wild mouse *Mus dunni* (LANDER, M. R. and CHATTOPADHYAY, S. K. (1984) *J. Virol.* 52, 695–698); Fischer rat embryo (FRE) cells (SCOLNICK, E. M. et al. (1976) *J. Virol.* 20, 570–582); and NIH/3T3 cells (JAINCHILL, J. L. et al. (1969) *J. Virol.* 4, 549–553). All were grown in RPMI-1640 medium supplemented with $5 \times 10^{-5}$ M 2-mercaptoethanol (2-ME) and 10% fetal calf serum (FCS).

The X63-Ag8.653 myeloma cell line (KEARNEY, J. F. et al. (1979) *J. Immunol.* 123, 1548–1550) used in hybridoma production was originally obtained from ATCC and was maintained at Rocky Mountain Laboratories in DME with 4.5 gm/l of glucose supplemented with $5 \times 10^{-5}$ M 2-ME, 2 mM glutamine, 0.1 mg/ml gentamicin, and 10% FCS which had been selected for a high cloning efficiency of hybridomas.

Viruses. A recombinant vaccinia virus, P4-4,expressing the gp85 protein of the F-MuLV strain 57 env gene was described previously (EARL, P. L. et al. (1986) *Science* 234, 728–731). The F-MuLV strain used in most studies was the molecular clone FB29 (SITBON, M. et al. (1986) *Cell* 47, 851–859). Cell-free viral stocks of FB29 were prepared from chronically infected Dunni cells. Stocks of B-tropic Friend virus complex (FV-B), containing both replication competent F-MuLV as well as the defective spleen focus forming virus (SFFV), were prepared as spleen homogenates from infected BALB/c mice as previously described (CHESEBRO, B. et al. (1974) *J. Exp. Med.* 140, 1457–1467).

Dunni cells, NIH/3T3 cells, or FRE cells infected with the following MuLV's were also used: ectropic F-MuLV strains 57 (OLIFF, A. I. et al. (1980) *J. Virol.* 33, 475–486) and B3 (LINEMEYER, D. L. et al. (1980) *J. Virol.* 35, 710–721); ecotropic Moloney-MuLV strain 1387 (LINEMEYER, D. L. et al. (1981) *Proc. Natl. Acad. Sci. USA* 78, 1401–1405);

ecotropic AKR-MuLV strain 1/5 (CHATTOPADHYAY, S. K. et al. (1981) *Virology* 113, 465–483); xenotropic-MuLV strains BALB/IU-1 (HARTLEY, J. W. and ROWE, W. P. (1976) *J. Virol.* 19, 19–25), AKR-6, and C58 L1 (CHATTOPADHYAY, S. K. et al. (1981) *Virology* 113, 465–483); and amphotropic-MuLV strain 1504A (HARTLEY, J. W. and ROWE, W. P. (1976) *J. Virol.* 19, 19–25). Recombinant MCF viruses were also tested. MCF viruses have been shown to be generated in vivo by the recombination of ectropic sequences with endogenous, polytropic sequences during the course of infection with ecotropic viruses. MCF viruses derived from F-MuLV that were tested included strains F-MCF-FrNX (ADACHI, A. et al. (1984) *J. Virol.* 50, 813–821), F-MCF-98D13 (BULLER, R. S. et al. (1990) *J. Virol.* 64, 493–498), and F-MCF-1T (TROXLER, D. H. et al. (1978) *J. Exp. Med.* 148, 639–653). The MCF viruses derived from Moloney-MuLV that were tested included strains MN2P-Sa, MN2P-Tb, MN7P-Ta, MN7P-Tb; and the MCF viruses derived from AKR-MuLV were strains M73P-S, M60P-T, M72P-S, M75P-T (EVANS, L. H. and MALIK, F. G. (1987) *J. Virol.* 61, 1882–1892). Cells chronically infected with each virus were passaged as needed and seeded to sub-confluence in a 24 well tissue culture plate (Linbro, Flow Laboratories, McLean, Va.) the day before screening with monoclonal antibodies.

Hybridoma Production. (B10.A(2R)×A.BY)$F_1$ mice were immunized by tail scratch with $1\times10^7$ PFU of recombinant vaccinia virus P4-4, then boosted with $1\times10^7$ PFU given intraperitoneally 4 weeks later. Three days after the booster inoculation, spleen and lymph nodes were harvested and fused with the X63-Ag8.653 myeloma cell line using the method described by DE ST. GROTH, F. & SCHEIDEGGER ((1980) *J. Immunol. Methods* 35, 1–21). When wells showed obvious cell growth, supernatant fluid was screened for antibodies.

Screening Hybridomas. Dunni cells chronically infected with F-MuLV were used to screen the hybridomas. Uninfected Dunni cells were used as a negative control. $5\times10^3$ cells were added to each well of a 96 well flat-bottomed tissue culture plate and allowed to grow overnight. The next day the supernatant was removed, and 100 µl of methanol was added to each well. After 5 minutes the methanol was removed by shaking the trays over a sink, and the trays were immediately immersed in TNE buffer (10 mM Tris-HCl, pH 8.0, 150 mM NaCl, 2 mM EDTA). Immediately before use the buffer was discarded, and each well was washed once with 100 µl TNE containing 1% FCS. After discarding the wash, 100 µl of tissue culture supernatant from the hybridomas was added and allowed to incubate for one hour at room temperature. Each well was then washed 4 times with 200 µl of TNE with 1% FCS. After the final wash, 50 µl of a 1/180 dilution of a horseradish peroxidase conjugated goat anti-mouse immunoglobulin antiserum (HRP goat anti-mouse IG)(Cappell, Organon Teknika, West Chester, Pa.) was added to each well and allowed to incubate at room temperature for 30 minutes. After washing the plates 4 times with TNE buffer, 100 µl of freshly prepared amino-ethyl-carbazol (AEC)-$H_2O_2$ solution was added as a substrate (Nexö, 1977). The stock solution of AEC (4 mg/ml) in dimethyl formamide was stored at −20° C. in the dark. Just prior to use 1 volume of this stock was added to 19 volumes of 0.05 M sodium acetate/acetic acid buffer, pH 5.0. Then 1 µl of stock 30% $H_2O_2$ was added per 2 ml solution, and this was mixed and added immediately to wells. The plates were incubated for 20 minutes in the dark then washed three times with tap water. The plates were allowed to dry and then viewed at 10×–20× magnification under a Nikon SMZ-10 dissecting microscope (Nikon, Tokyo, Japan); wells were scored as positive if the wells containing Dunni cells infected with F-MuLV were stained red but the plates with uninfected Dunni cells were colorless. Positive hybridoma wells were expanded and cloned in fibrin gel cultures as described below. Four stable hybridoma lines were obtained, subcloned, and further characterized.

Cloning Hybridomas in Fibrin Gels. Hybridomas were cloned in fibrin gels by a modification of the method described by Ohara and Watanabe (IWASAKI, T. et al. (1982) *Monoclonal antibodies: Hybridomas and ELISA*, (Kodansha, Ltd., Tokyo)). Briefly, a solution of fibrinogen was made by dissolving 250 mg of fibrinogen (Bovine Type IV, Sigma Chemical Co., St. Louis, Mo.) in 100 ml citrate/Tris buffered saline (C-TBS) (140 mM NaCl, 6.7 mM KCl, 0.7 mM Na citrate, 20 mM Tris base, pH 7.0). 0.5 ml of fibrinogen solution was added to each well of a 6 well tissue culture dish and mixed with 2 ml of medium containing 0.01 units/ml bovine thrombin (Sigma Chemical Co., St. Louis, Mo.). The dishes were incubated overnight at 37° C. to allow the solution to clot. The next day $5\times10^3$ hybridoma cells were suspended in 4 ml medium containing freshly added thrombin and 1 ml of freshly made fibrinogen solution. Two ten-fold dilutions of cells were made in the same solutions, and 1 ml of the cell suspensions were added on top of the fibrin clots made the previous day. The dishes were incubated at 37° C. in a 5% $CO_2$ incubator. After approximately one week, individual colonies of cells could be visualized. Colonies were picked using a sterile Pasteur pipette and were expanded in 24 well tissue culture plates.

Isotype Determination. The isotype of each of the subclones was determined by gel immunodiffusion using isotype specific antibodies (The Binding Site, Inc., San Diego, Calif.).

Specificity of Monoclonal Antibodies. In order to determine the viral specificity of the four monoclonal antibodies, each was tested against the panel of murine retroviruses listed above using both the indirect immunoperoxidase assay on fixed cells and the membrane immunofluorescence assay on live infected cells as previously described (CHESEBRO, B. et al. (1981) *Virology* 112, 131–144).

Radioimmunoprecipitation. The viral protein specificity of the monoclonal antibodies was determined by immunoprecipitation of F-MuLV antigens from $^{35}$S-methionine-labelled Dunni cells infected with F-MuLV, as previously described (CHESEBRO, B. et al. (1981) *Virology* 112, 131–144). For IgG1 antibodies, Sepharose-Protein A beads (Pharmacia, Piscataway, N.J.) were precoated with polyclonal rabbit anti-mouse Ig serum (Sigma Chemical Co., St. Louis, Mo.).

Western Blotting. F-MuLV particles were purified from pooled culture supernatant of Dunni cells chronically infected with F-MuLV by polyethylene glycol precipitation as previously described (MIYAZAWA, M. et al. (1987) *J. Exp. Med.* 166, 890–908). Viral proteins were separated on a 12.5% SDS-PAGE gel (AUSUBEL, F. et al. (1989) *Current Protocols in Molecular Biology*, Green Publishing Associates and Wiley-Interscience, N.Y.) with and without 2-mercaptoethanol present in the sample buffer, then electroblotted onto an Immobilon filter (Millipore, Bedford, Mass.), using standard buffer (TOWBIN, H. et al. (1979) *Proc. Natl. Acad. Sci. USA* 76, 4350–4354) supplemented with 0.01% SDS. The filter was blocked with 5% nonfat dried milk in TBST (10 mM Tris-HCl, pH 8.0, 150 mM NaCl, and 0.05% Tween 20). The filter was then cut into strips, and these were incubated with 2 ml of hybridoma tissue culture supernatant for 1 hour at room temperature. After washing three times in TBST, the strips were reacted with alkaline phosphate-conjugated goat anti-mouse Ig serum (Sigma Chemical Co., St. Louis, Mo.) for 1 hour, washed three times in TBST, then reacted with substrate (ProtoBlot AP, Promega, Madison, Wis.).

Focal Infectivity Assay. The antibodies were tested in a focal infectivity assay (FIA) as previously described (Sitbon et al. 1985). Dunni cells were seeded at $1 \times 10^4$ cells per well in a 24 well tissue culture plate and allowed to grow overnight. The next day serial three-fold dilutions of culture supernatant from Dunni cells chronically infected with F-MuLV, or diluted serum from Friend virus-infected mice, were added to each well in the presence of 8 µg/ml polybrene. The cells were incubated for 2 hours at 37° C., then the media was changed. The cells were allowed to grow for an additional 48 hours, then fixed with methanol for 5 minutes and stored under TNE buffer. Foci of infected cells were detected by the indirect immunoperoxidase method using monoclonal antibody hybridoma tissue culture supernatant as the first antibody. After final development, foci of red cells were counted under a dissecting microscope.

Biotinylation of Antibody 720. Antibody 720 was purified and concentrated by passing two liters of tissue culture supernatant over a 5 ml packed volume Protein G-Sepharose column (Pharmacia, Piscataway, N.J.). The antibody was eluted, then biotinylated using a solution of N-hydroxysuccinimide biotin (Sigma Chemical Co., St. Louis, Mo.) (HARLOW, E. and LANE, D. (1988) *Antibodies: A Laboratory Manual*, Cold Spring Harbor Laboratory, Cold Spring Harbor, N.Y.).

Electron Microscopy of Glutaraldehyde-fixed Tissue Culture Cells. For immunoelectronmicroscopy, cells were grown in 60 mm tissue culture dishes (Permanox, Miles Laboratories, Naperville, Ill.) overnight. Two dishes were seeded with $1 \times 10^6$ Dunni cells infected with F-MuLV, and two dishes were seeded with the same number of FRE cells infected with the 1504A isolate of amphotropic-MuLV (HARTLEY, J. W. and ROWE, W. P. (1976) *J. Virol.* 19, 19–25). The next day the cells were fixed with freshly prepared 2% glutaraldehyde (BDH Limited, Poole, England), then washed 3 times with 2 ml Dulbecco's phosphate buffered saline (D-PBS) (140 mM NaCl, 8 mM $Na_2HPO_4$, 2.7 mM KCl, 1.5 mM $KH_2PO_4$, pH 7.2). Free aldehyde groups were blocked with 100 mM glycine in D-PBS, and the cells were washed again with D-PBS. One ml of antibody 720 was added to a dish of Dunni cells infected with F-MuLV and to a dish of FRE cells infected with amphotropic-MuLV. As a control, the previously described antibody, 83A25 (EVANS, L. H. et al. (1990) *J. Virol.* 64), which reacts with amphotropic-MuLV but not F-MuLV, was added to the other dish of each virus-infected cell type. The antibodies were allowed to incubate with the cells for 1 hour at room temperature. The dishes were washed 4 times with D-PBS with 1% FCS, then incubated for one hour with 0.2 ml of gold-conjugated goat anti-mouse immunoglobulin antiserum (Cappel, Organon Teknika, West Chester, Pa.) at room temperature with rocking. After washing 4 times as above, the cells were reacted with 1% $OsO_4/K_3Fe(CN)_3$ for 30 minutes, washed twice with 0.1 M sodium cacodylate buffer, pH 7.5, and then stained with 1% aqueous uranyl acetate, pH 3.9, for 15 minutes. After washing twice with tap water, the dishes were flooded with 0.1% tannic acid in distilled water for 15 minutes, rinsed twice with distilled water, then dehydrated in increasing concentrations (30%, 60%, 90%) of cold acetone for 5 minutes at each concentration. The cells were then dehydrated for 90 minutes in 100% acetone. Acetone was replaced with 100% Spurr's resin (Polyscience, Warrington, Pa.) for 4 hours, then fresh 100% Spurr's resin was added and allowed to stand overnight. The sides of the dishes were cut with a razor blade and the embedded monolayer released from the bottoms of the dishes. Sections of the planchettes containing the embedded cells were sawed out with a jeweler's saw and glued together with adhesive cyanoacrylate glue with the monolayers in apposition to each other. These blocks, containing two layers of cells back-to-back, were then reduced in size to fit a BEEM capsule (Ted Pella, Inc., Redding, Calif.) and reembedded in Spurr's resin as above. After polymerization, the monolayers were sectioned in an orientation perpendicular to the plane of the cell layer. This cross-sectional cut allowed for surface-to-base visualization of the cells and of viral particles budding from the cell surfaces. Post-staining was with uranyl acetate and lead citrate. Photography was done using a Hitachi HU-11E-1 electron microscope operating at 75 kV.

Immunohistochemistry on tissue sections. In one experiment BALB/c mice were inoculated intravenously with 150 spleen focus forming units of Friend virus complex. Ten days later the animals were sacrificed, their spleens removed, and sections of the bone marrow were obtained. In another experiment, neonatal IRW mice were inoculated intraperitoneally with F-MuLV strain FB29, and on day 10 post infection the mice were sacrificed and tissue sections obtained from the brain. In both experiments the tissue was immediately frozen in Tissue-Tek O.C.T. compound (Miles, Inc., Elkhart, Ind.). Frozen sections were made using a Reichart Histostat microtome and fixed in cold (4° C.) acetone. Biotinylated antibody 720 was used to detect viral antigens in the tissue sections as previously described (MORI, S. et al. (1990) *Microbial Pathogenesis* 9, 243–253) using an HRP-avidin detection system (ABC Kit PK-4000, Vector Laboratories, Burlingame, Calif.). The sections were viewed at 40× magnification on an Olympus BH-2 microscope (Olympus, Tokyo, Japan).

Example 1

Generation and Characterization of Envelope-specific Monoclonal Antibodies

To elicit an immune response specific for the envelope of F-MuLV, mice were immunized by tail scratch with a recombinant vaccinia virus expressing the gp85 envelope protein of F-MuLV. Four weeks later the mice were boosted with the same recombinant vaccinia virus intraperitoneally. Three days after the booster inoculation the animals were sacrificed and their spleen and lymph nodes harvested. Hybridomas were made using standard techniques, and then screened for reactivity with methanol-fixed, chronically infected tissue culture cells. After final cloning, four distinct monoclonal antibodies of the following isotypes were obtained: 720, IgG1; 721, IgG2a; 722, IgG1; and 723, IgG3.

The monoclonal antibodies were screened against a panel of murine retroviruses to determine their viral specificity. Each was found to react with all three ecotropic F-MuLV strains tested (FB29, 57, and B3) and with two polytropic, recombinant MCF viruses (F-MCF-FrNX and F-MCF-98D13) containing F-MuLV sequences in the C-terminal one-third of gp70 (FIG. 1). In contrast, F-MCF-1T, also derived from F-MuLV but containing polytropic sequences throughout gp70, did not react with any of the monoclonal antibodies. There was no reactivity with the other murine retroviruses tested, including ecotropic AKR-MuLV, ecotropic Moloney-MuLV, amphotropic MuLV, and xenotropic- MuLV, nor with polytropic MCF viruses derived from Moloney-MuLV or AKR-MuLV. These data suggested that the epitope(s) recognized by each of the four antibodies was in the C-terminal one-third of F-MuLV gp70.

Figure 2:
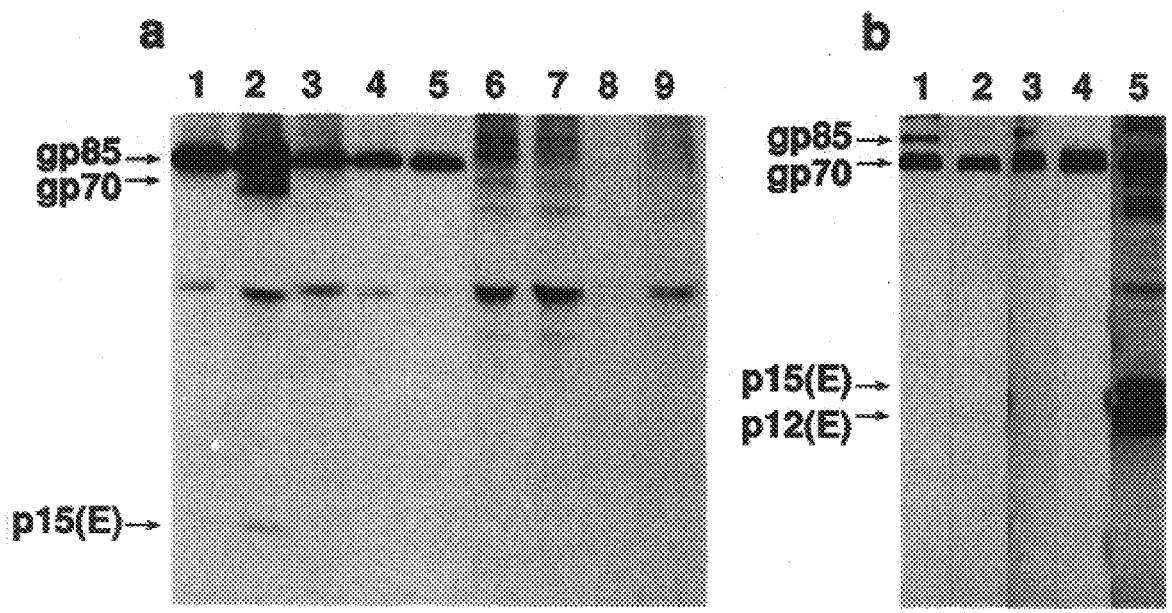
FIGS. 2(a) and 2(b). Immunoprecipitation of $^{35}$S-methionine-labelled viral proteins by monoclonal antibodies. Lanes 1–5: Dunni cells chronically infected with F-MuLV strain FB29. Lanes 6–9: Uninfected Dunni cells. Lane 1: antibody 48 (CHESEBRO, B. et al. (1983a). Virology 127, 134–148). Lanes 2 and 6: antibody 720. Lanes 3 and 7: antibody 721. Lanes 4 and 8: antibody 722. Lanes 5 and 9: antibody 723. (b) Western blotting of purified F-MuLV particles separated by SDS-PAGE under non-reducing conditions (lanes 1 and 3) or under reducing conditions (lanes 2, 4 and 5) to break the disulfide linkage between gp70 and p15(E). Lanes 1 and 2: Anti-gp70 monoclonal antibody 307 (CHESEBRO, B. et al. (1981). Virology 112, 131–144). Lanes 3 and 4: Antibody 720. Lane 5: Polyclonal anti-gp85 rabbit serum. Antibody 720 reacted with both the gp85 envelope precursor protein and gp70 in the absence of 2-ME (lane 3), but under reducing conditions (lane 4) only gp70 is recognized, similar to the previously described IgM monoclonal antibody 307 (CHESEBRO, B. et al. (1981). Virology 112, 131–144). Polyclonal anti-gp85 rabbit serum cross reacts with gp70 and p15(E) in the presence of 2-ME.

Each antibody was then used to immunoprecipitate viral proteins from cell lysates of Dunni cells infected with F-MuLV which had been labelled with $^{35}$S-methionine. Each of the antibodies reacted with the gp85 envelope precursor protein, and bands corresponding to gp70 and p15(E) could also be clearly visualized after precipitation with antibody 720 (FIG. 2a). Because gp70 and p15(E) are disulfide-linked in the detergent lysate (PINTER, A. and HONNEN, W. J. (1989) Virology 173, 136–143) and thus precipitate together, antibody 720 was used for Western blotting of viral antigens under both reducing and non-reducing conditions to determine which protein was recognized by antibody 720. Under non-reducing conditions, antibody 720 reacted with both the gp85 precursor protein and gp70, but in the presence of 2-ME, only gp70 was recognized (FIG. 2b). This indicated that antibody 720 recognized the gp70 portion of gp85.

Example 2

Focal Infectivity Assay

Figure 3:
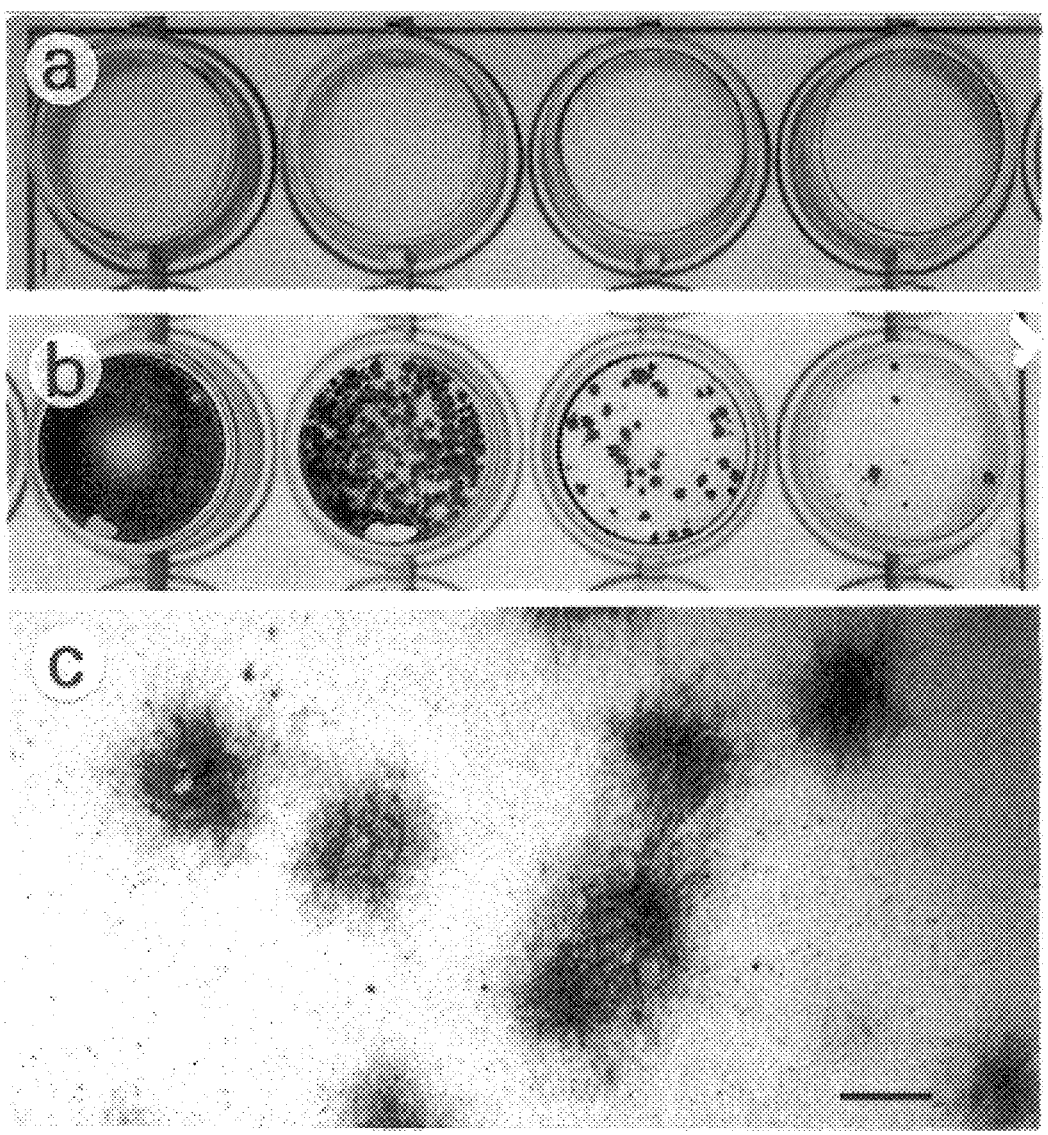
FIGS. 3(a) and 3(b). Dunni cells were infected with serial three fold dilutions of F-MuLV for 48 hours, then fixed with methanol. The top row of wells was stained with antibody 48, the bottom row with antibody 720. (b) Close up view of foci under a dissecting microscope.

Monoclonal antibodies have been used to quantitate murine retroviruses in a focal infectivity assay on live cells (CHESEBRO, B. et al. (1983a) Virology 127, 134–148). The antibodies described here were generated to determine if a similar assay could be performed on fixed cell. Antibody 720 was selected for testing since it gave the strongest staining on fixed F-MuLV infected cells. As seen in FIG. 3a, antibody 720 could be used in the focal infectivity assay when the cells were fixed with methanol prior to staining, whereas the previously described antibody 48 (CHESEBRO, B. et al. (1983a) Virology 127, 134–148) did not react with methanol-fixed cells. The foci detected by antibody 720 were visible macroscopically, and when examined under a dissecting microscope at low magnification (FIG. 3b), small foci could easily be counted. Because an entire well can be visualized in a single field at low magnification, the peroxidase method was much simpler and more reliable than counting foci of live cells at the higher magnifications needed to see the foci with the membrane immunofluorescence. Assays performed on infected cells which had been fixed and stored under TNE buffer for several days before adding the primary antibody gave results comparable to assays which were processed immediately.

Example 3

Electron Microscopy on Infected Tissue Culture Cell

Figure 4:
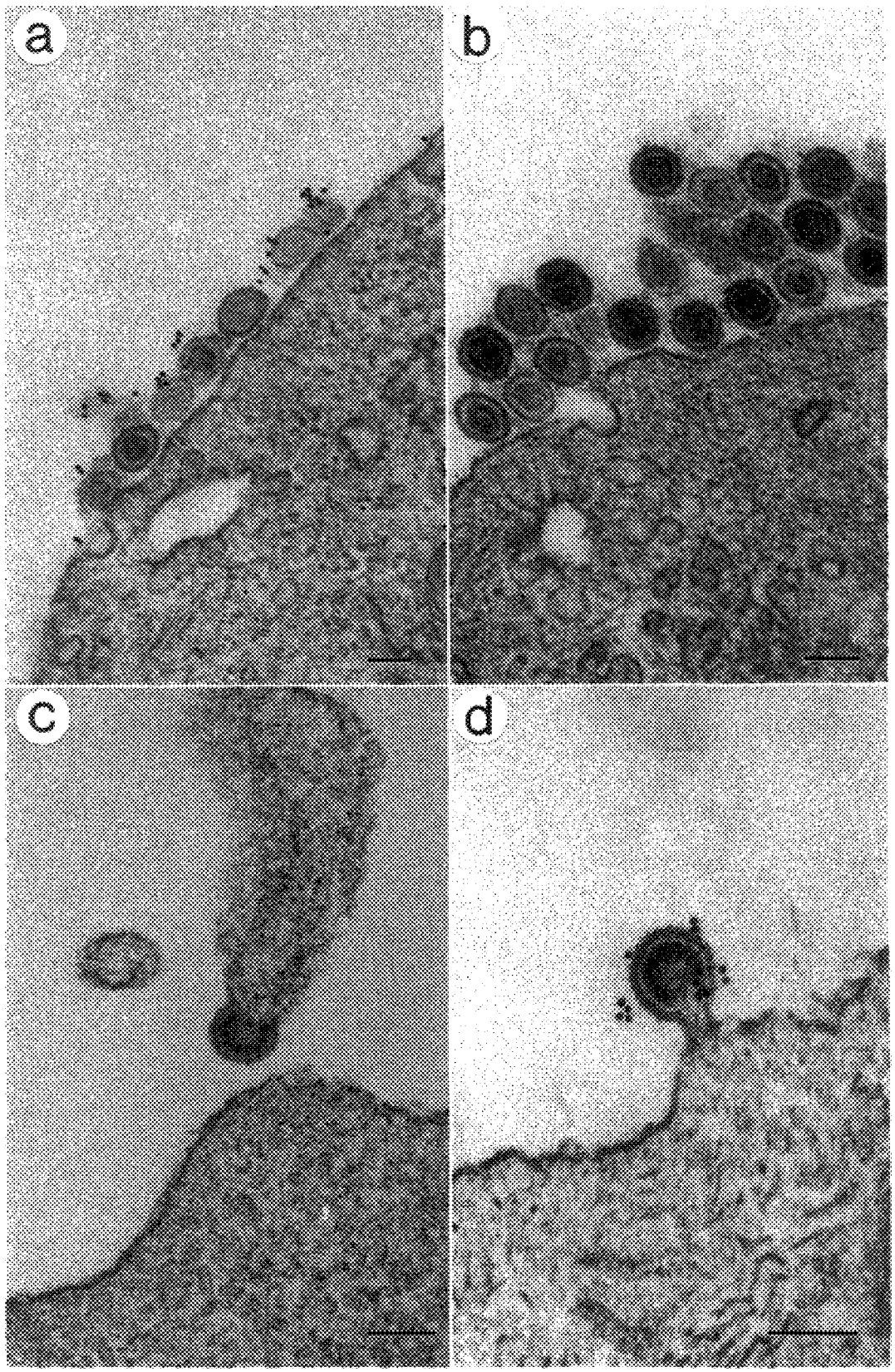
FIGS. 4(a), 4(b), 4(c) and 4(d). Immunoelectronmicrograph of cells infected with F-MuLV or amphotropic MuLV. (a) Dunni cells infected with F-MuLV then stained with antibody 720. Free viral particles and viral particles budding from the surface of infected cells (arrow) are labelled with grains of gold. Bar represents 100 nm. (b) Dunni cells infected with F-MuLV reacted with antibody 83A25 (EVANS, L. H. et al. (1990) J. Virol. 64), which does not react with F-MuLV. Viral particles are seen, but are not labelled with gold. (c) FRE cells infected with amphotropic MuLV do not label with gold when antibody 720 is used as the first antibody, but do label when (d) 83A25 is used.

Retroviral particles in infected cells can often be demonstrated by electron microscopy, and the morphological appearance of such retroviruses has been used as the basis of one virus classification scheme (WEISS, R. et al. (1984) RNA Tumor Viruses, Cold Spring Harbor Laboratory, Cold Spring Harbor, N.Y.). In many in vivo studies it would be highly desirable to be able to identify individual retroviruses at the electron microscope level. However, specific viruses cannot be distinguished on morphological grounds alone. In contrast, detection of viral proteins using specific monoclonal antibodies can distinguish many types of murine retroviruses in complex mixtures (SITBON, M. et al. (1985) Virology 141, 110–118). Because antibody 720 was capable of detecting F-MuLV envelope in infected tissue culture cells after fixation with glutaraldehyde, which is commonly used to fix tissues for electron microscopy, this antibody was used for immunoelectronmicroscopy. Tissue culture cells infected with either F-MuLV or amphotropic-MuLV were fixed with glutaraldehyde, incubated with antibody 720, reacted with a gold-conjugated second antibody specific for mouse immunoglobulin, and then examined by electron microscopy. As a control, the same virus-infected tissue culture cells were also stained with the previously described antibody 83A25, which reacts with amphotropic-MuLV but not F-MuLV (EVANS, L. H. and MALIK, F. G. (1987) J. Virol. 61, 1882–1892). Free viral particles and viral particles budding from the surface of cells infected with F-MuLV were specifically labelled with gold particles when antibody 720 was used as the first antibody (FIG. 4a) but not when antibody 83A25 was used (FIG. 4b). Conversely, amphotropic-MuLV particles were not labelled when antibody 720 was used as the first antibody (FIG. 4c) but were labelled when antibody 83A25 was used (FIG. 4d).

Example 4

Immunohistochemistry

Figure 5:
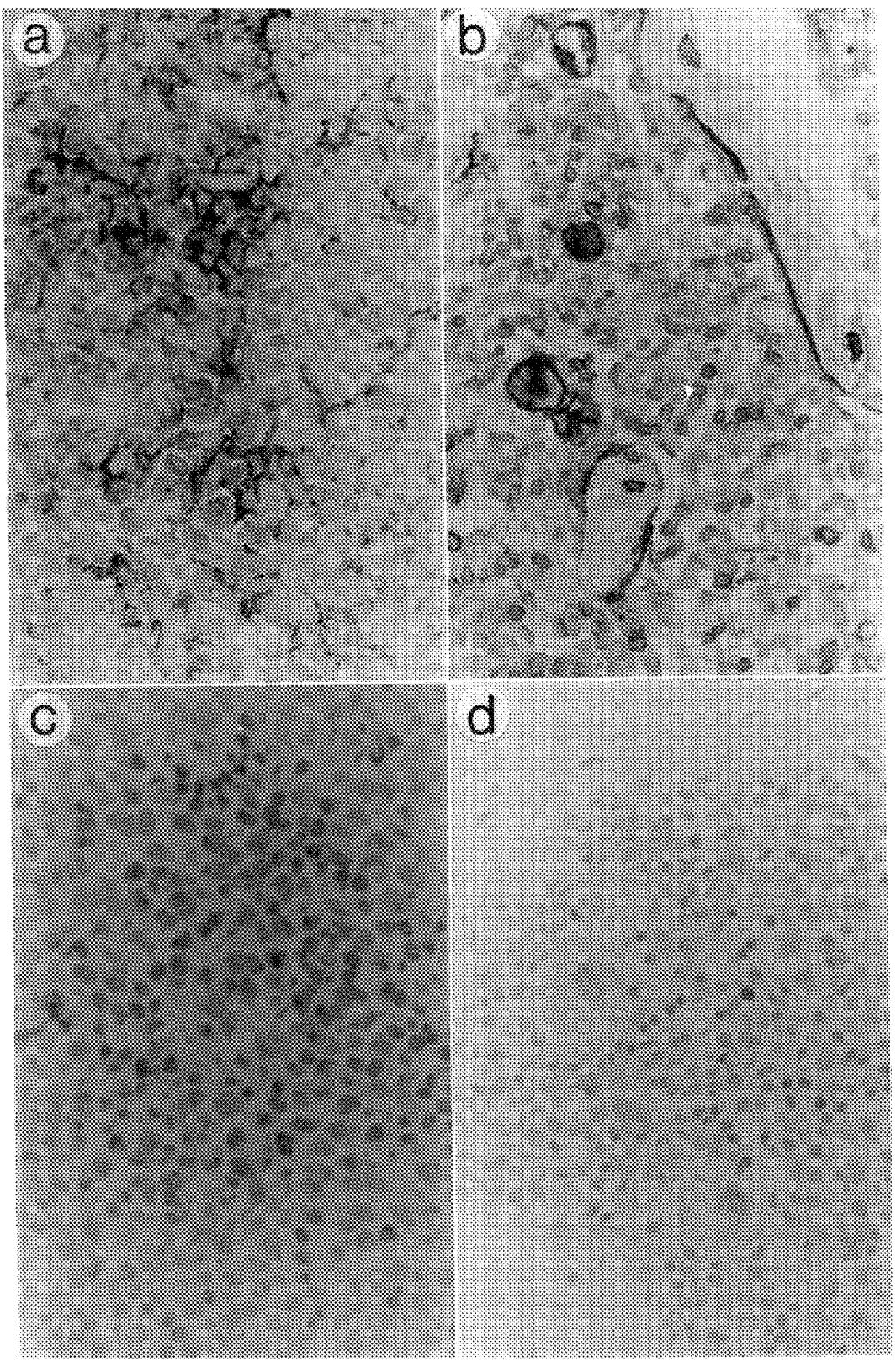
FIGS. 5(a), 5(b), 5(c) and 5(d). Immunohistochemistry of fixed tissue sections from BALB/c mice. (a) Spleen and (b) bone marrow from a mouse 10 days after infection with F-MuLV. (c) Spleen and (d) bone marrow of an uninfected littermate. Tissue sections were prepared and stained using biotinylated antibody 720.

Light microscopy has also been used to detect viral antigens in the tissues of infected animals. However, F-MuLV, like many other retroviruses, replicates in lymphoid tissues, and the presence of immunoglobulin bearing cells in these tissues prevents the use of conventional indirect immunostaining techniques which use peroxidase-conjugated anti-mouse immunoglobulin reagents. To overcome this problem antibody 720 was biotinylated and used in combination with a peroxidase-avidin detection system to examine spleen (FIG. 5a) and bone marrow (FIG. 5b) from mice acutely infected with F-MuLV. In both tissues megakaryocytes and small cells, probably erythroid precursors, were seen to be infected. Cells in the osteoid of the bone marrow were also stained (FIG. 5b). These cells had the morphology of osteoblasts. In uninfected control animals, neither spleen (FIG. 5c) nor bone marrow (FIG. 5d) exhibited any staining. Thus, biotinylated antibody 720 was capable of detecting virus-infected cells in lymphoid tissues.

Figure 6:
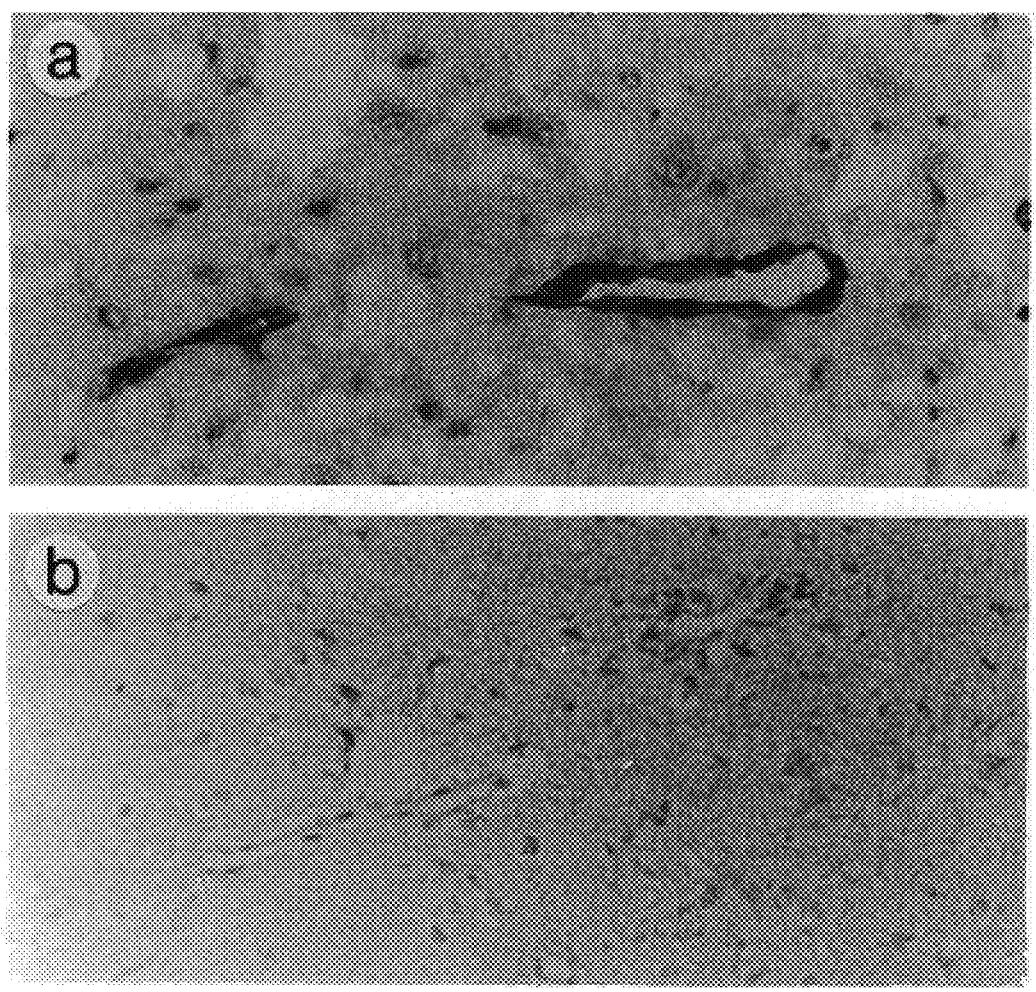
FIGS. 6(a) and 6(b). Frozen sections of brain tissue stained with biotinylated antibody 720 after acetone fixation. (a) IRW mouse neonatally infected with F-MuLV. Tissue was obtained 10 days post infection. (b) Uninfected IRW mouse brain section.

F-MuLV has also been reported to replicate in the central nervous system (CNS) (GARDNER, M. B. et al. (1973) J. Nat. Cancer Inst. 51, 1243–1254). Antibody 720 was used to stain acetone-fixed frozen sections of brain and spinal cord from infected mice. In these experiments brain capillary endothelial cells of infected mice stained intensely (FIG. 6a). No staining of neurons or of glial cells was seen. Uninfected control animals had no staining of any cells (FIG. 6b). Thus, antibody 720 was capable of detecting F-MuLV antigens in CNS tissue.

Deposit of Biological Material

The hybridoma cell line designated 720 was deposited with the American Type Culture Collection, 10801 University Boulevard, Manassas, Va. 20100-2209 on Oct. 10, 2001 and assigned ATCC No. PTA-3774.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A hybridoma which produces a Friend murine leukemia virus (F-MuLV) specific monoclonal antibody specific for an antigenic determinant of a gp85 envelope precursor protein characteristic of a methanol-fixed F-MuLV infected cell.

2. The hybridoma according to claim 1, wherein said hybridoma results from the fusion of a myeloma cell and a spleen cell.

3. The hybridoma according to claim 2 wherein said myeloma cell is derived from a mouse.

4. The hybridoma according to claim 3 wherein said myeloma cell is X63-Ag8.653.

5. A hybridoma producing monoclonal antibody 720, IgG1 having ATCC No. PTA-3774.

6. A monoclonal antibody specific for an antigenic determinant of a gp85 envelope precursor protein characteristic of a Friend Murine Leukemia virus infected cell, which antigenic determinant specifically binds the monoclonal antibody produced by the hybridoma according to claim 5, or a binding fragment thereof.

7. A diagnostic kit comprising a conjugate comprising:
   i) at least one mononclonal antibody according to claim 6, and
   ii) a label.

8. A Friend murine leukemia virus (F-MuLV) specific monoclonal antibody, or binding fragment thereof, specific for an antigenic determinant of a gp85 envelope precursor protein characteristic of a methanol-fixed F-MuLV infected cell.

9. The monoclonal antibody according to claim 8 wherein said antibody is of the IgG class.

10. A diagnostic kit comprising a conjugate comprising:
    i) at least one monoclonal antibody according to claim 8, and
    ii) a label.

* * * * *